US00PP18144P2

(12) United States Plant Patent
Schoenmakers

(10) Patent No.: US PP18,144 P2
(45) Date of Patent: Oct. 23, 2007

(54) ***PEPEROMIA* PLANT NAMED 'SILVER SHADOW'**

(50) Latin Name: *Peperomia orba*
Varietal Denomination: Silver Shadow

(75) Inventor: Kees Schoenmakers, Haaren (NL)

(73) Assignee: Schoenmakers Tropische Potcultures VOF, Haaren (NL)

( * ) Notice: Subject to any disclaimer, the term of this patent is extended or adjusted under 35 U.S.C. 154(b) by 8 days.

(21) Appl. No.: 11/287,063

(22) Filed: Nov. 25, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell

(57) ABSTRACT

A new cultivar of *Peperomia* plant named 'Silver Shadow' that is characterized by a broad upright growth habit and white and green leaves.

1 Drawing Sheet

Botanical classification: *Peperomia orba.*
Variety denomination: 'Silver Shadow'.

BACKGROUND OF THE INVENTION

The present invention relates to a new and distinct cultivar of *Peperomia* plant botanically known as *Peperomia orba* and hereinafter referred to by the cultivar name 'Silver Shadow'.

'Silver Shadow' was discovered as a naturally occurring whole plant mutation of *Peperomia orba* 'Variegeta'. The new cultivar was discovered by the inventor in a cultivated area of Haaren, The Netherlands in February 2004.

Asexual reproduction by terminal cuttings of the new cultivar 'Silver Shadow' was first done in June 2004 in Haaren, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Peperomia* cultivar 'Silver Shadow'.

1. *Peperomia* 'Silver Shadow' exhibits white and green leaves.
2. *Peperomia* 'Silver Shadow' exhibits a broad upright growth habit.

The closest comparison cultivar is the parent plant *Peperomia orba* 'Variegeta'. 'Silver Shadow' is distinguishable from 'Variegeta' by the following characteristics:

1. 'Silver Shadow' has white and green leaves. The leaves of 'Variegeta' are yellow and green.

BRIEF DESCRIPTION OF THE DRAWING

The accompanying photograph illustrates the distinguishing traits of *Peperomia* 'Silver Shadow'. The plant in the photograph shows an overall view of a 12 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Peperomia* cultivar named 'Silver Shadow'. Data was collected in Haaren, The Netherlands from 12 week old greenhouse grown plants in 8.5 cm. containers. The time of year was Fall and the average daytime and nighttime temperatures were 23° Centigrade. The light level was natural outdoor light and there were no photoperiodic treatments. Color determinations are in accordance with The Royal Horticultural Society Colour Chart 2001 edition, except where general color terms of ordinary dictionary significance are used. The growing requirements are similar to the species. 'Silver Shadow' has not been tested under all possible conditions and phenotypic differences may be observed with variations in environmental, climatic, and cultural conditions, however, without any variance in genotype.

Botanical classification: *Peperomia orba* 'Silver Shadow'.
Use: Ornamental Perennial.
Parentage: 'Silver Shadow' is a naturally occurring whole plant mutation of *Peperomia orba* 'Variegeta'.
Vigor: Low.
Growth rate: Approximately 2 cm. per month.
Growth habit: Broad upright.
Plant shape: Flattened globular.
Suitable container size: 8.5 cm. container.
Height: Average 10 cm. in height.
Width: Average 12.3 cm. in width.
Hardiness: Zone 10.
Propagation: Cuttings.
Time to initiate roots: Approximately 21 days to produce roots on an initial cutting.
Time to produce a rooted cutting or liner: Approximately 35 days.
Root system: Fine and fibrous.
Stem:
*Branching habit.*—Freely branching.
*Average number of lateral branches.*—4.
*Pinching.*—No.
*Lateral branch diameter.*—4 mm. in diameter.
*Lateral branch length.*—4.2 cm. in length.
*Lateral branch color.*—194B with dots of 185C.

*Stem color.*—138B to 144B with small dots and stripes, 185B to 185C.
*Pubescence.*—Dense, length 0.5 mm, color N155A.
*Internode length.*—1.4 cm. between nodes.
*Shape.*—Rounded.
*Surface.*—Glossy.
*Stem strength.*—Strong.

Foliage:
*Texture.*—Glossy.
*Leaf arrangement.*—Alternate.
*Compound or single.*—Single.
*Quantity of leaves per lateral branch.*—7.
*Leaf shape.*—Cordate.
*Leaf apex.*—Acute.
*Leaf base.*—Rounded.
*Leaf length.*—4 cm. in length.
*Leaf width.*—2.2 cm. in width.
*Pubescence.*—Dense, transparent, length 0.2 mm.
*Leaf margin.*—Entire.
*Vein pattern.*—Pinnate.
*Young leaf color* (*upper surface*).—137B, margins 145C to 150D.
*Young leaf color* (*lower surface*).—191B, margins 150D.
*Mature leaf color* (*upper surface*).—138A to 191A with irregular blotches and margins 192B to 193A to 193B, and also 157D to 155A.
*Mature leaf color (lower surface).*—191C to 191D.
*Vein color* (*lower surface*).—138B.
*Vein color* (*upper surface*).—138B.
*Leaf attachment.*—Petiolate.
*Petiole dimensions.*—1.9 cm. in length and 3 mm. in diameter.
*Petiole color.*—148D.
*Durability of foliage to stress.*—Moderate to high.

Flower:
*Flower arrangement.*—Stalked terminal spike.
*Inflorescence type.*—Spike.
*Inflorescence dimensions.*—2 mm. in diameter and 3.5 cm. in height.
*Flowering habit.*—Continuously.
*Quantity of spikes per inflorescence.*—1.
*Quantity of flowers per spike.*—Over 1,500.
*Quantity of flower buds per spike.*—Over 1,500.
*Quantity of flowers and buds per plant.*—Over 1,500.
*Flowering season.*—Autumn.
*Rate of flower opening.*—Approximately 75% of the flowers are opened at one stage.
*Fragrance.*—None.
*Flower bud length.*—0.3 mm. in length.
*Flower bud diameter.*—0.3 mm. in diameter.
*Flower bud shape.*—Flattened.
*Bud color.*—151B.
*Rate of bud opening.*—7 days per bud.
*Flower aspect.*—Upright to slightly outward.
*Flower shape.*—Rotate.
*Flower dimensions.*—Average 0.5 mm. in diameter and 0.2 mm. in height.
*Flower longevity.*—Lasts approximately 14 days on plant.
*Self-cleaning or persistent.*—Persistent.
*Bracts.*—Absent.

Peduncle:
*Peduncle length.*—4 mm.
*Peduncle diameter.*—2.5 mm.
*Peduncle angle.*—30° from stem.
*Peduncle strength.*—Moderate.
*Peduncle color.*—138B to 144B with small dots and stripes, 185B to 185C.
*Pedicels.*—Absent.

Reproduction organs:
*Stamen number.*—2.
*Anther shape.*—Kidney-shaped.
*Anther size.*—0.1 mm.
*Anther color.*—N186D.
*Amount of pollen.*—Low.
*Pollen color.*—157A.
*Pistil number.*—1.
*Pistil dimensions.*—1 mm. in length.
*Stigma shape.*—Terete.
*Stigma color.*—153A.
*Style length.*—0.2 mm.
*Style color.*—153A.
*Ovary color.*—153A.

Seed: Seed production has not been observed.

Disease and pest resistance: Plants of the new *Peperomia* have not been observed for disease or pest resistance.

It is claimed:

1. A new and distinct variety of *Peperomia* plant named 'Silver Shadow' as described and illustrated.

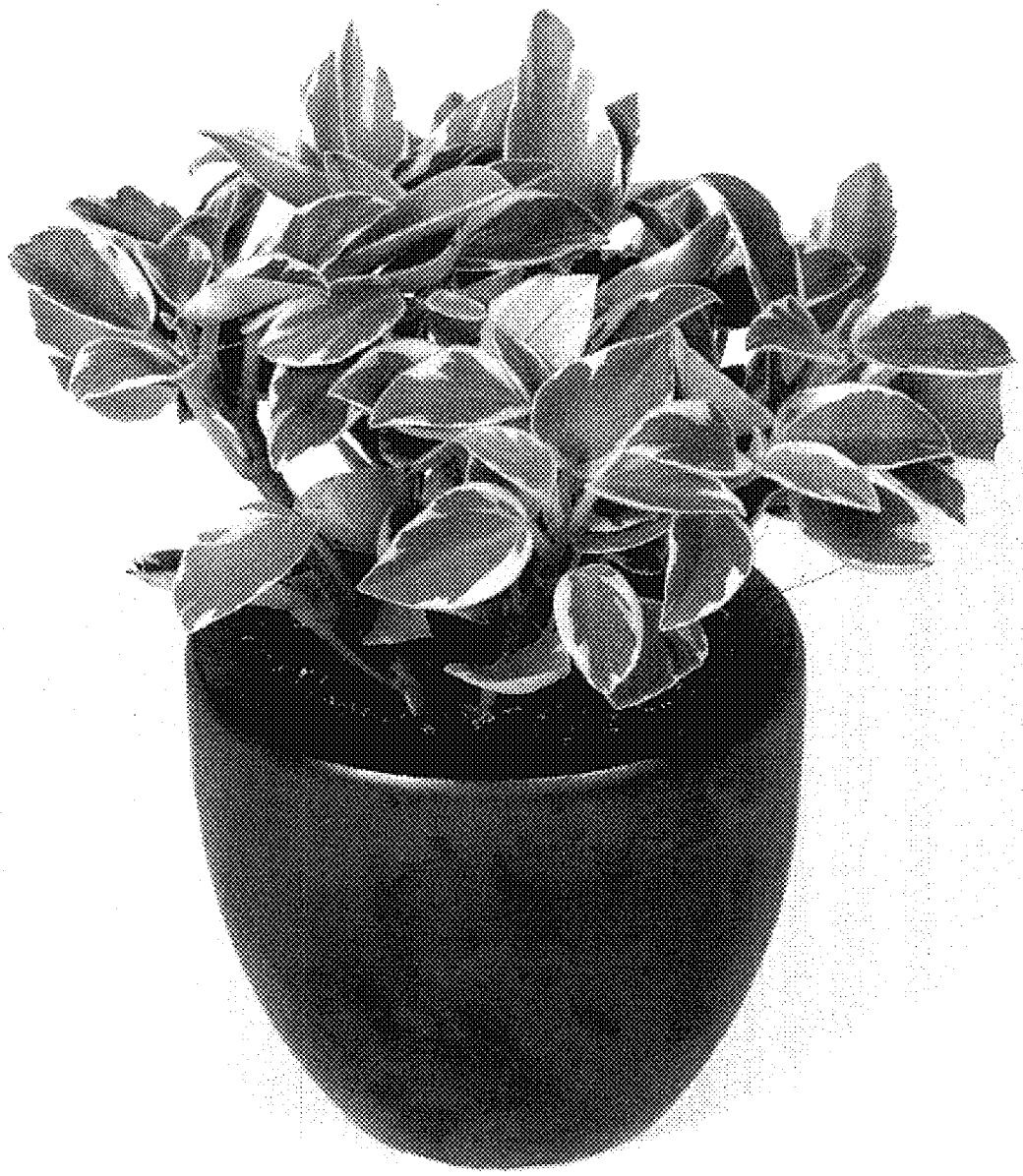

* * * * *